United States Patent
Serafini et al.

[11] Patent Number: 6,110,711
[45] Date of Patent: Aug. 29, 2000

[54] METHOD OF DEFINING CELL TYPES BY PROBING COMPREHENSIVE EXPRESSION LIBRARIES WITH AMPLIFIED RNA

[75] Inventors: Tito Serafini, San Francisco; John Ngai, Berkeley, both of Calif.

[73] Assignee: The Regents of the University of California, Oakland, Calif.

[21] Appl. No.: 09/212,338

[22] Filed: Dec. 15, 1998

Related U.S. Application Data

[63] Continuation-in-part of application No. 09/049,664, Mar. 27, 1998, abandoned.
[60] Provisional application No. 60/069,589, Dec. 12, 1997.
[51] Int. Cl.[7] .......................... C12P 19/34; C07H 21/02; C07H 21/04; C12Q 1/68
[52] U.S. Cl. .......................... 435/91.21; 435/6; 435/91.2; 536/23.1; 536/24.31; 536/24.33
[58] Field of Search .......................... 435/6, 91.2, 91.21; 536/23.1, 24.31, 24.33

[56] References Cited

U.S. PATENT DOCUMENTS

| | | | |
|---|---|---|---|
| 5,514,545 | 5/1996 | Eberwine et al. | 435/6 |
| 5,716,785 | 2/1998 | Barchas et al. | |

FOREIGN PATENT DOCUMENTS

| | | |
|---|---|---|
| 91/18115 | 11/1991 | WIPO . |
| 95/08647 | 3/1995 | WIPO . |
| 96/14435 | 5/1996 | WIPO . |
| 97/26333 | 7/1997 | WIPO . |

OTHER PUBLICATIONS

Zhao et al Gene vol. 156 pp. 207–213, 1995.
Hara et al NAR vol. 19, No. 25, pp. 7097–7104, 1991.
Mosser et al Biotechniques vol. 222 pp. 150–161, 1997.
Brady et al Method in Mol. Cell. Biol. vol. 2 pp. 17–25, 1990.
Liu et al NAR vol. 21, No. 21 pp. 4954–4960, 1993.

Crino et al., "Embryonic Neuronal Markers in Tuberous Sclerosis: Single–Cell Molecular Pathology". PNAS, vol. 93, 1996, pp. 14152–14157.

Cheetham et al., "Isolation of Single Immunohistochemically Identified Whole Neuronal Cell Bodies From Post––Mortem Human Brain for Simultaneous Analysis of Multiple Gene Expression". Journal of Neuroscience Methods, vol. 77, No. 1, Nov. 1997, pp. 43–48.

Toellner et al., "The Use of Reverse Transcription Polymerase Chain Reaction to Analyse Large Numbers of MRNA Species from a Single Cell". Journal of Immunological Methods, vol. 191, 1996, pp. 71–75.

Wildner, et al., "Generation of a Conditionally neo(r)–Containing Retroviral Producer Cell Line: Effects of neo(r) on Retroviral Titer and Transgene Expression". Gene Therapy, vol. 5, 1998 pp. 684–691.

Chow et al., "Expression Profiles of Multiple Genes in Single Neurons of Alzheimer's Disease". PNAS, vol. 95, Aug. 1998, pp. 9620–9625.

*Primary Examiner*—Kenneth R. Horlick
*Assistant Examiner*—Jeffrey Siew
*Attorney, Agent, or Firm*—Richard Aron Osman

[57] ABSTRACT

The invention provides methods and compositions for defining a cell type, generally involving the steps of (a) amplifying the mRNA of a single cell of a heterogenous population of cells; (b) probing a comprehensive expression library with the amplified mRNA to define a gross expression profile of the cell; and (c) comparing the gross expression profile of the cell with a gross expression profile of one or more other cells to define a unique expression profile of the cell, wherein the unique expression profile of the cell provides a marker defining the cell type.

21 Claims, 4 Drawing Sheets

METHOD OF DEFINING CELL TYPES BY PROBING COMPREHENSIVE EXPRESSION LIBRARIES WITH AMPLIFIED RNA

CROSS REFERENCE TO RELATED APPLICATION

This application is a Continuation in Part of and claims priority under 35USC120 to application Ser. No. 09/049,664, filed Mar. 27, 1998, now abandoned which claims priority to U.S. Provisional Application Ser. No. 60/069,589 filed Dec. 12, 1997 by Tito Serafini, Percy Luu, John Ngai and David Lin and entitled Methods for Amplifying Nucleic Acids. This application is also related to copending U.S. application Ser. No. 09/049,806, filed Mar. 27, 1998 by Tito Serafini, Percy Luu, John Ngai and David Lin and entitled Methods for Making Nucleic Acids.

The disclosed inventions were made with Government support under Grant (Contract) No. 1RO1DC02253 awarded by the National Institutes of Health. The government may have rights in these inventions.

INTRODUCTION

1. Field of the Invention

The field of this invention is defining markers for cell types.

2. Background

The identity of a cell is a direct manifestation of the specific complement of genes that it expresses from among the 50,000 to 100,000 genes in the genome. Because individual cell types usually exist to perform specific functions within the organism, a technology that defines cell types through gene expression would not only permit us to assign the expression of genes to functionally defined cell types, but it would also enable us more easily to discover genes imparting functionally relevant properties to individual cells. This assignment of function to gene sequences is a major goal of the field of genomics.

A technology to identify distinct cell types systematically based upon patterns of gene expression would therefore permit very useful, functionally important definitions of cells. Approaches to such a technology have usually involved performing pairwise comparisons of expressed genes from different cell types (for example, differential display or subtractive hybridization). A shortcoming of such approaches is the impracticality of using pairwise comparisons to identify numerous cell types in a complex tissue. Furthermore, such approaches usually rely upon the ability to isolate cells as pure populations, a situation that does not exist for most cell types in most tissues. Technologies are also needed that would allow the identification of cell types without knowing in advance that they exist. In the human brain, for example, neurons have historically been defined by parameters such as morphology, position, connectivity, and the expression of a small number of marker genes. However, we do not know how many intrinsically different cell types exist in the brain, what functional differences most of these cell types have, and how these differences are manifested in the expression of specific genes. A solution to a problem of this magnitude requires development of new technologies. We describe such a technology here.

Relevant Literature

Sippel (1973) Eur.J.Biochem. 37, 31–40 discloses the characterization of an ATP:RNA adenyltransferase from *E. coli* and Wittmann et al. (1997) Biochim.Biophys.Acta 1350, 293–305 disclose the characterization of a mammalian poly(A) polymerase. Gething et al. (1980) Nature 287, 301–306 disclose the use of an ATP:RNA adenyltransferase to polyadenylate the '3 termini of total influenza virus RNA. Eberwine et al. (1996) U.S. Pat. No. 5,514,545 describes a method for characterizing single cells based on RNA amplification. Eberwine et al. (1992) Proc.Natl.Acad.Sci USA 89, 3010–3014, describe the analysis of gene expression in single live neurons. Gubler U and Hoffman BJ. (1983) Gene (2–3), 263–9, describe a method for generating cDNA libraries, see also the more recent reviews, Gubler (1987) Methods in Enzymology, 152, 325–329 and Gubler (1987) Methods in Enzymology, 152, 330–335. Clontech (Palo Alto, Calif.) produces a "Capfinder" cloning kit that uses "GGG" primers against nascent cDNAs capped with reverse transcriptase, Clontechniques 11, 2–3 (October 1996), see also Maleszka et al. (1997) Gene 202, 39–43.

SUMMARY OF THE INVENTION

The invention provides methods and compositions for defining a cell type. The general methods involve the steps of (a) amplifying the mRNA of a single cell of a heterogenous population of cells; (b) probing a comprehensive expression library with the amplified mRNA to define a gross expression profile of the cell; and (c) comparing the gross expression profile of the cell with a gross expression profile of one or more other cells to define a unique expression profile of the cell, wherein the unique expression profile of the cell provides a marker defining the cell type. In particular embodiments, step (c) comprises comparing the gross expression profile of the cell with a gross expression profile of (i) a plurality of other cells to define a unique expression profile of the cell; (ii) a plurality of other single cells to define a unique expression profile of the cell; and/or (iii) a plurality of gross expression profiles of each of a plurality of other single cells to define a unique expression profile of the cell, and the plurality of other single cells are derived from a functionally or structurally distinct subpopulation of cells. Accordingly, the invention may involve the steps of: (a) defining a heterogenous subpopulation of cells of an organism; (b) constructing a comprehensive library from the mRNA of the subpopulation of cells; (c) amplifying the mRNA of a single cell of the population; and (d) probing the library with the amplified mRNA to define gene expression of the cell, wherein the gene expression of the cell provides a marker defining the cell type.

The subpopulation of cells comprises a discernable group of cells sharing a common characteristic. For example, the subpopulation may comprise tissue-specific cells, e.g. hippocampal neurons, cells presenting a common marker, such as CD8+ cells, etc. In one embodiment, the marker derives from a common mutation, particularly where the mutation is an inserted genetic construct which encodes and provides each cell with a common selectable marker, such as an epitope or signal-producing protein. In a preferred embodiment, the inserted construct further encodes and provides each cell an internal ribosome entry sequence and the construct is inserted into a target gene downstream of the stop codon but upstream of the polyadenylation signal in the last exon of the target gene, such that the internal ribosome entry sequence provides a second open reading frame within a transcript of the target gene. Selection and/or separation of the target subpopulation may be effected by any convenient method. For example, where the marker is an externally accessible, cell-surface associated protein or other epitope-containing molecule, immuno-adsorption panning techniques or fluorescent immuno-labeling coupled with fluorescence activated cell sorting are conveniently applied.

The probed library is typically a cDNA library, preferably normalized or subtracted. In a particular embodiment, the library comprises a high density ordered array of immobilized nucleic acids.

The mRNA may be amplified by any technique applicable to a single cell. In a particular embodiment, the amplification is a linear method comprising the steps of adding a known nucleotide sequence to the 3' end of a first RNA having a known sequence at the 5' end to form a second RNA and reverse transcribing the second RNA to form a cDNA.

Finally, the library is probed with the amplified mRNA to determine gene expression of the subject cell wherein unique gene expression or gene expression patterns provide markers for defining the cell type.

DETAILED DESCRIPTION OF PREFERRED EMBODIMENTS OF THE INVENTION

Figure 1:
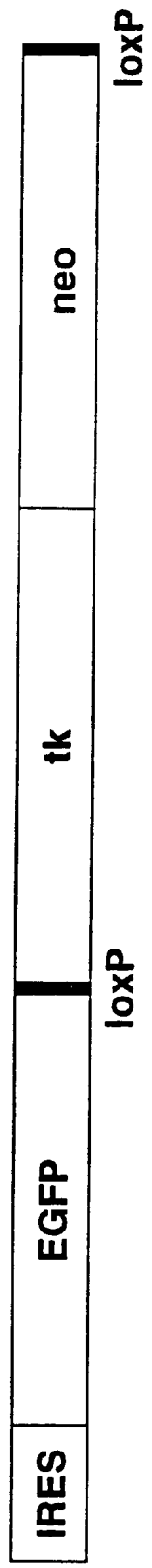
FIG. 1 is a schematic of a cassette containing an internal ribosome entry sequence (IRES).

The following preferred embodiments and examples are offered by way of illustration and not by way of limitation.

We describe a technology for identifying and ultimately isolating distinct cell types in a heterogenous population of interest by defining the genes expressed in different cells. First, a heterogeneous cell population, generally present as a subset of the cells in a tissue and defined by the common expression of a gene important for the function of the particular group of cells, is defined. In one embodiment, this is accomplished by using the endogenous promoter of such a gene to express a green fluorescent protein (GFP) in transgenic cells, and the targeted population of cells isolated with flow cytometry. A cDNA library, optionally normalized and/or subtracted, is then made from these cells and arrayed. Hybridization probes are made by amplifying the mRNA of individual cells from the heterogeneous pool of cells and hybridized separately to the arrayed cDNA clones. Through the analysis of differences in hybridization to the arrayed cDNA clones, groups of co-expressed transcripts restricted to specific cell types within the heterogenous population of cells are identified and used to define those cell types.

There are numerous applications of this technology, including the isolation of individual cell populations for which no markers yet exist, e.g for designing drugs targeted to discrete cell populations. Also, the ability to define and isolate novel cell types facilitates the discovery and characterization of novel trophic molecules. Additionally, the technology permits the assignment of particularized function to gene sequences, allowing, for example the production of antibodies and transgenic animals that permit the manipulation of individual cell types.

The invention can be applied to any tissue in which the degree of cellular heterogeneity is not known, or where morphologically defined cell types have been described but lack molecular markers. Importantly, such new markers for different cell types enables a range of applications; for example, such markers allow individual cell types to be isolated through antibodies to cell-surface antigens encoded by marker genes or through transgenic approaches that label cells expressing such genes. This ability to isolate, in pure form, different types of cells from a complex tissue permits a range of applications, including identification of cell-type-specific trophic molecules. Being able to isolate the individual cell types comprising a related group of cells also provides precise targets for testing therapeutic agents, permitting the more facile generation of compounds that have desired effects on a target cell type while minimizing side effects generated through action on non-targets. For example, the abnormal functioning of subsets of serotonergic neurons has been implicated in a variety of mood disorders. However, drugs presently in use to treat these disorders affect all serotonergic neurons, often leading to undesirable side effects. The present invention provides a means to identify the specific subset of these neurons involved in a particular disorder, providing much better targets for the development of therapeutic agents specific for that subset of cells.

Accordingly, one aim of this technology is to delineate and identify distinct cell types in a heterogeneous population through the identification of differentially expressed genes. In general terms, these methods involve:

(1) Amplifying the mRNA of a single cell of a heterogenous population of cells, preferably using the amplification technique described below;

(2) Probing a comprehensive expression library with the amplified mRNA to define a gross expression profile of the cell; and (3) Comparing the gross expression profile of the cell with a gross expression profile of one or more other cells to define a unique expression profile of the cell, wherein the unique expression profile of the cell provides a marker defining the cell type. In other words, defining the cell type by probing the arrayed population cDNA library with the amplified mRNA populations, e.g. to identify sets of transcribed genes that define an "expression fingerprint" for a particular cell type.

Amplifying the mRNA population of single cells. Suitable methods for amplifying the mRNA population of single cells include the Brady and Iscove method (Brady et al., 1990, Methods Mol & Cell Biol 2, 17–25), based upon exponential, PCR-based amplification of relatively short, extreme 3' stretches of mRNA molecules, and methods that use linear, RNA-polymerase based amplification, e.g. the Eberwine protocol (Eberwine et al. (1992) Proc.Natl.Acad-.Sci USA 89, 3010–3014). However, for most applications, we favor a linear, RNA-polymerase based amplification method described below. Linear amplification introduces fewer biases during amplification than exponential amplification, giving a greater certainty of finding differentially expressed genes represented by low abundance transcripts, and the amplification of the original mRNA population using the entire procedure is on the order of 1,000,000-fold.

Probing a comprehensive expression library. The probed library will generally represent all genes expressed by an organism or a subpopulation of cells thereof, preferably a functionally or structurally distinct subpopulation of cells thereof, such as cells of a given tissue, cells expressing one or more common genes, etc. Defining subpopulation by expression of a common gene is facilitated by using homologous recombination and a marker gene. In particular, in order to drive expression from an endogenous promoter without decreasing the endogenous levels of gene product, we insert the cassette shown in FIG. 1 into the gene of interest using homologous recombination. The internal ribosome entry sequence (IRES), derived from the encephalomyocarditis virus, permits the initiation of translation at a second open reading frame within a single mRNA molecule. The IRES-GFP cassette is introduced by standard techniques downstream of the stop codon but upstream of the polyadenylation signal in the last exon of the gene of interest. Generation and screening of ES cell clones, and generation of transgenic animals from these clones are performed using standard techniques. In order to prevent complications from the presence of the promoter driving neo expression, we eliminate our lox-site-delimited neo expression fragment through transient transfection of ES cells with a plasmid encoding Cre recombinase. Immunohistochemistry is used to verify that GFP is confined to cells expressing the gene of interest and flow cytometric sorting to isolate GFP$^+$ cells. In many applications, we use a modified GFP, EGFP, which has an excitation maximum at 488 nm, matching the output of the laser in a flow cytometer.

The comprehensive expression library is preferably normalized and presented in a high density array. For example, we isolate mRNA from purified GFP$^+$ cells and construct a plasmid cDNA library using standard procedures. Because approximately one tenth (1000–2000 out of 15,000–20,000) of the mRNA species in a typical somatic cell constitute 50–65% of the mRNA present, we normalize our cDNA library using reassociation-kinetics-based methods, e.g. Soares MB (1997) Curr Opin Biotechnol 8(5):542–546 and citations therein. While not always required, we find that normalizing the library both increases the frequency of discovering large numbers of differentially expressed genes (increasing the utility of our fingerprints to identify both cell types and cell-type specific genes) and minimizes the amount of screening required. This normalization method has successfully been used to normalize cDNA libraries such that the abundance of all cDNA species falls within an order of magnitude, while preserving the representation of the longest cDNAs. Additionally, cross-hybridizing diverged sequences generally escape normalization in this procedure. Probing the library provides a gross expression profile of the cell representing all the genes expressed by the cell and present in the comprehensive library.

Comparing the gross expression profiles (identifying cell types and cell-type-specific gene expression). We use these amplified mRNA populations from single cells to generate probes to screen the arrayed comprehensive expression library. The arrayed library works as a "DNA spectrograph": All arrayed nucleic acids are potential targets, but only those expressed in an individual cell register as positive after hybridization. The pattern of hybridizing messages provides an "expression fingerprint" that defines a cell type, while the exact cDNAs that hybridize are marker genes for that cell type. Any arraying of the library that allows the library to be screened by hybridization functions may be used. Typically, such arraying involves robotic picking and spotting on nylon or glass support matrices using microarraying technologies, e.g. Heller R., et al. (1997) Proc Natl Acad Sci USA, 94, 2150–2155.

Figure 2:
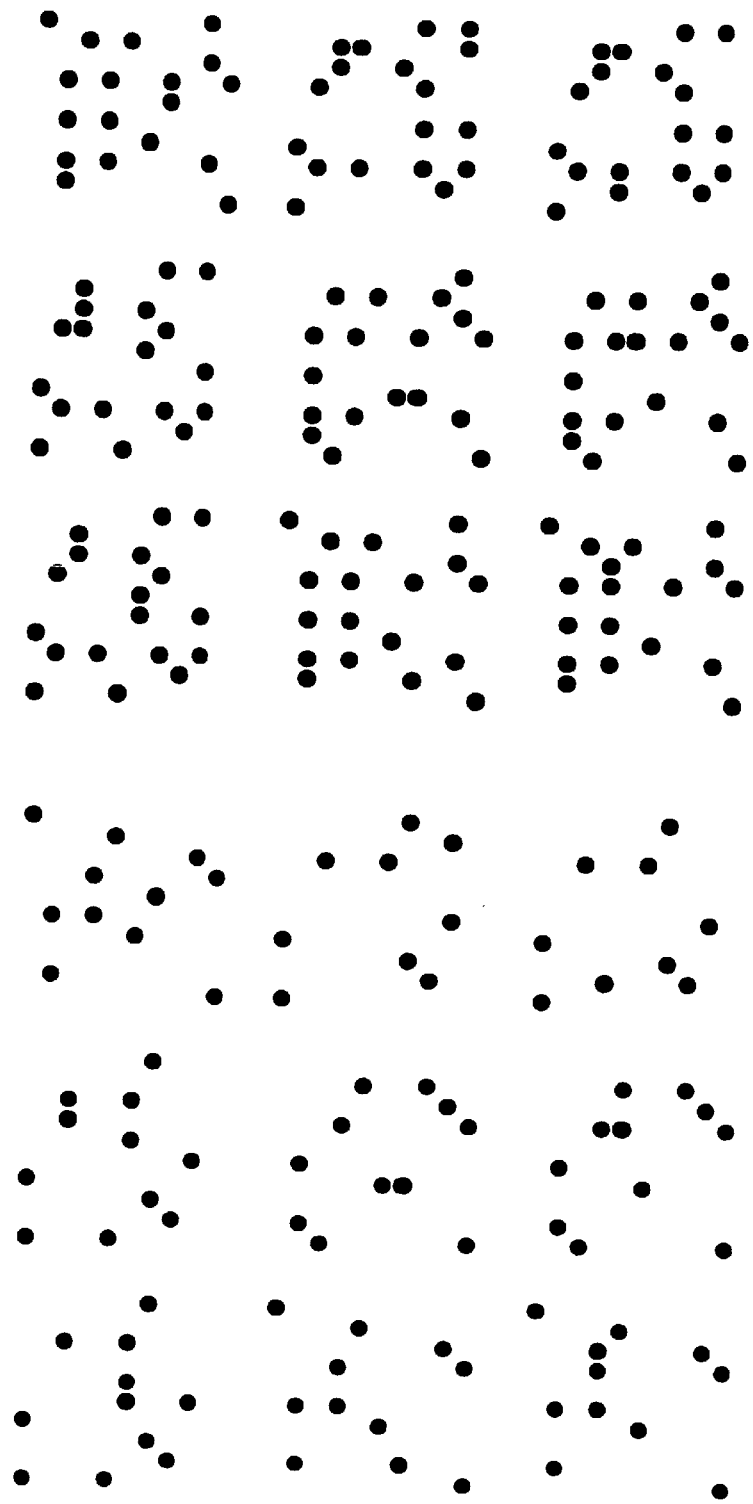
FIG. 2 is a schematic of results for a cDNA array screened with individual single-cell probes.

After capture, the hybridization signals generated by individual single-cell probes are analyzed manually or, preferably using automated techniques, e.g. Wodicka L, et al. (1997) Nat Biotechnol 15(13):1359–1367; Zweiger G, (1997) Curr Opin Biotechnol 8(6):684–687, and citations therein. This comparing or analysis step frequently comprises comparing the gross expression profile of the cell with a gross expression profile of (i) a plurality of other cells to define a unique expression profile of the cell; (ii) a plurality of other single cells to define a unique expression profile of the cell; and/or (iii) a plurality of gross expression profiles of each of a plurality of other single cells to define a unique expression profile of the cell, and the plurality of other single cells are derived from a functionally or structurally distinct subpopulation of cells. For example, one analysis consists of determining the frequencies with which individual genes are expressed together in individual cells. FIG. 2 presents a schematic of results for a one-hundred-element array screened nine times with individual single-cell probes. After analyzing the hybridization patterns (top panel), we find several different classes of expressed genes (bottom panel). While a few genes are expressed randomly as a result of noise, some variation is detectable as a result of activity-dependent effects on gene expression, and some genes are expressed at high frequencies in all cells, we are able to define core groups of genes that are expressed together repeatedly in some cases and not others. These sets of genes define individual cell-types. Our analysis also yields other genes that are expressed with the highly correlated sets of genes only in some cases. These groups define functional subtypes; for example, such genes may be patterning genes that confer positional identity to otherwise identical cell types. cDNAs that identify cell types are partially sequenced and matched against GenBank and Mouse EST Project databases. Novel cDNAs are entirely sequenced for further analysis. In situ hybridization with probes derived from selected cDNAs are used to verify correlated expression of genes in a single cell type within the tissue of origin.

Amplification methodology. The preferred amplification methods generally comprise the steps of adding a known nucleotide sequence to the 3' end of a first RNA having a known sequence at the 5' end to form a second RNA and reverse transcribing the second RNA to form a cDNA. The known sequence at the 5' end of the first RNA species is sufficient to provide a target for a primer and otherwise determined largely by the nature of the starting material. For example, where the starting material is mRNA, the known sequence at the 5' end may comprise a poly(A) sequence and/or (b) an internal mRNA sequence of an mRNA. Alternatively, where the starting material is amplified RNA, or aRNA, the known sequence may comprise a poly(T) sequence or the complement of a known internal mRNA sequence. The known 5' sequence may advantageously comprise additional sequences such as primer target sites, RNA polymerase sites, etc. For example, the presence of both a primer target site such as a poly(T) sequence and an RNA polymerase promoter sequence permits enhanced opportunities for downstream amplification or transcription.

The adding step may be effect by any convenient method. For example, a polyadenyltransferase or poly(A) polymerase may be used to add selected nucleotides to the 3' end. Poly(A) polymerases may be derived from a wide variety of prokaryotic and eukaryotic sources, are commercially available and well-characterized. In another example, a ligase may be used to add one or more selected oligonucleotides. These enzymes are similarly readily and widely available from a wide variety of sources and are well characterized.

The added known 3' sequence is similarly sufficient to provide a target for a primer, otherwise the nature of the added known sequence is a matter of convenience, limited only by the addition method. For example, using ligase mediated oligonucleotide addition, essentially any known sequence that can be used as target for a primer may be added to the 3' end. With polyadenyltransferase mediated addition, it is generally more convenient to add a poly(N) sequence, with many such transferases demonstrating optimal efficiency when adding poly(A) sequence. For polyadenyltransferase mediated additions, the added sequence will generally be in the range of 5 to 50 nucleotides, preferably in the range of 6 to 25 nucleotides, more preferably in the range of 7 to 15 nucleotides.

The reverse transcribing step is initiated at a noncovalently joined duplex region at or near the 3' end of the second RNA species (the first species with the added 3' sequence), generally formed by adding a primer having sufficient complementarity to the 3' end sequence to hybridize thereto. Hence, where the 3' end comprises a poly(A) sequence, the reverse transcribing step is preferably initiated at a duplex region comprising a poly(T) sequence hybridized to the poly(A) sequence. For many applications, the primer comprises additional functional sequence such as one or more RNA polymerase promoter sequences such as a T7 or T3 RNA polymerase promoter, one or more primer sequences, etc.

In a preferred embodiment, the RNA polymerase promoter sequence is a T7 RNA polymerase promoter sequence comprising at least nucleotides −17 to +6 of a wild-type T7 RNA polymerase promoter sequence, preferably joined to at least 20, preferably at least 30 nucleotides of upstream flanking sequence, particularly upstream T7 RNA polymerase promoter flanking sequence. Additional downstream flanking sequence, particularly downstream T7 RNA polymerase promoter flanking sequence, e.g. nucleotides +7 to +10, may also be advantageously used. For example, in one particular embodiment, the promoter comprises nucleotides −50 to +10 of a natural class III T7 RNA polymerase promoter sequence. Table 1 provides exemplary promoter sequences and their relative transcriptional efficiencies in the subject methods (the recited promoter sequences are joined to a 23 nucleotide natural class III T7 promoter upstream flanking sequence).

TABLE I

Transcriptional efficiency of T7 RNA polymerase promoter sequences.

| Promoter Sequence | Transcriptional Efficiency |
| --- | --- |
| T AAT ACG ACT CAC TAT AGG GAG A (SEQ ID NO: 1, class III T7 RNA polymerase promoter) | ++++ |
| T AAT ACG ACT CAC TAT AGG CGC (SEQ ID NO: 2, Eberwine et al. (1992) supra) | + |
| T AAT ACG ACT CAC TAT AGG GCG A (SEQ ID NO: 3, Bluescript, Stratagene, La Jolla, CA) | + |

The transcribed cDNA is initially single-stranded and may be isolated from the second RNA by any of wide variety of established methods. For example, the method may involve treating the RNA with a nuclease such as RNase H, a denaturant such as heat or an alkali, etc., and/or separating the strands electrophoretically. The second strand cDNA synthesis may be effected by a number of well established techniques including 3'-terminal hairpin loop priming or methods wherein the polymerization is initiated at a noncovalently joined duplex region, generated for example, by adding exogenous primer complementary to the 3' end of the first cDNA strand or in the course of the Hoffman-Gubler protocol. In this latter embodiment, the cDNA isolation and conversion to double-stranded cDNA steps may be effected together, e.g. contacting the RNA with an RNase H and contacting the single-stranded cDNA with a DNA polymerase in a single incubation step. In any event, these methods can be used to construct cDNA libraries from very small, e.g. single cell, starting materials.

In a particular embodiment, the methods further comprise the step of repeatedly transcribing the single or double-stranded cDNA to form a plurality of third RNAs, in effect, amplifying the first RNA species. Preferred transcription conditions employ a class III T7 promoter sequence (SEQ ID NO:1) and a T7 RNA polymerase under the following reaction conditions: 40 mM Tris pH 7.9, 6 mM $MgCl_2$, 2 mM Spermidine, 10 mM DTT, 2 mM NTP (Pharmacia), 40 units RNAsin (Promega), 300–1000 units T7 RNA Polymerase (6.16 Prep). The enzyme is stored in 20 mM HEPES pH 7.5, 100 mM NaCl, 1 mM EDTA, 1 mM DTT and 50% Glycerol at a protein concentration of 2.5 mg/mL and an activity of 300–350 units/uL. In exemplary demonstrations, 1–3 uL of this polymerase was used in 50 uL reactions. Starting concentrations of template can vary from picogram quantities (single cell level) to 1 ug or more of linear plasmid DNA. The final NaCl concentration is preferably not higher than 6 mM.

Figure 3:
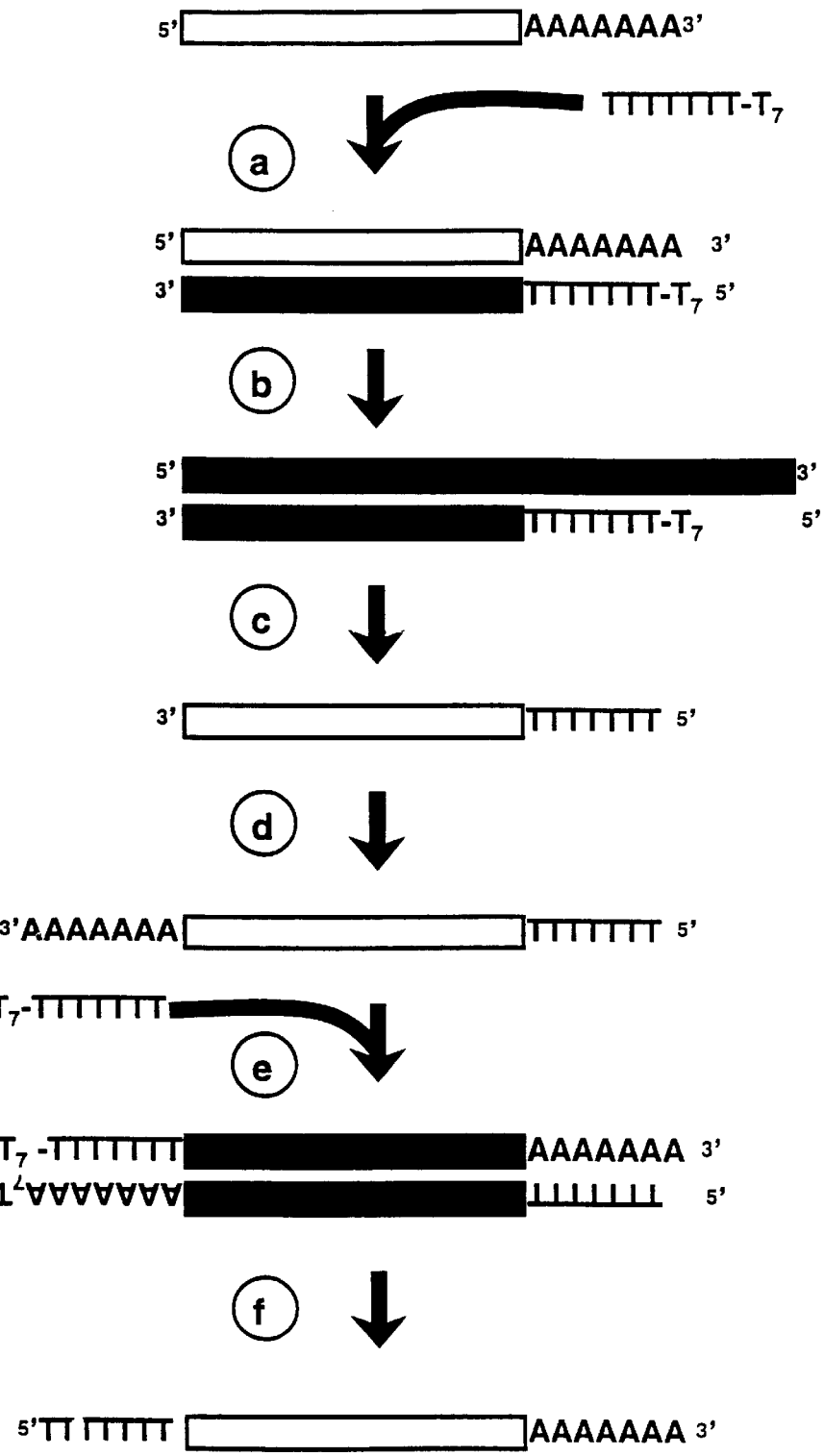
FIG. 3 is a schematic of a preferred mRNA amplification method.

In a more particular embodiment, the first RNA is itself made by amplifying an RNA, preferably a mRNA. For example, the first RNA may be made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA. FIG. 3 is a schematic of this serial mRNA amplification embodiment of the invention, highlighting individual steps of the method:

(a) An oligonucleotide primer, consisting of 5'-$T_7$-RNA polymerase promoter-oligo $(dT)_{24}$-3', is annealed to the poly(A) tract present at the 3' end of mature mRNAs, and first-strand cDNA is synthesized using reverse transcriptase, yielding an RNA-DNA hybrid (RNA is denoted by open boxes; DNA by filled boxes);

(b) The hybrid is treated with RNase H, DNA polymerase, and DNA ligase to convert the single-stranded cDNA into double-stranded cDNA;

(c) $T_7$ RNA polymerase is used to synthesize large amounts of amplified RNA (aRNA) from this cDNA. The incorporation of a modified $T_7$ polymerase promoter sequence into our primer, as compared to the altered promoter sequence utilized by Eberwine et al., PNAS 89: 3010–3014, 1992, greatly increases the yield of aRNA;

(d) The aRNA is tailed with poly(A) using a poly(A) polymerase. This modification generates much longer first-strand cDNA in the next step as compared to the original protocol;

(e) After denaturation and elimination of the aRNA, a $T_7$-RNA polymerase promoter-oligo (dT) primer is annealed to this newly synthesized poly(A) sequence, and reverse transcriptase is used to synthesize first-strand cDNA. Second-strand cDNA and the complementary strand of the polymerase promoter are synthesized as in (b); and (f) $T_7$ RNA polymerase is then used to generate aRNA from this cDNA template.

Figure 4:
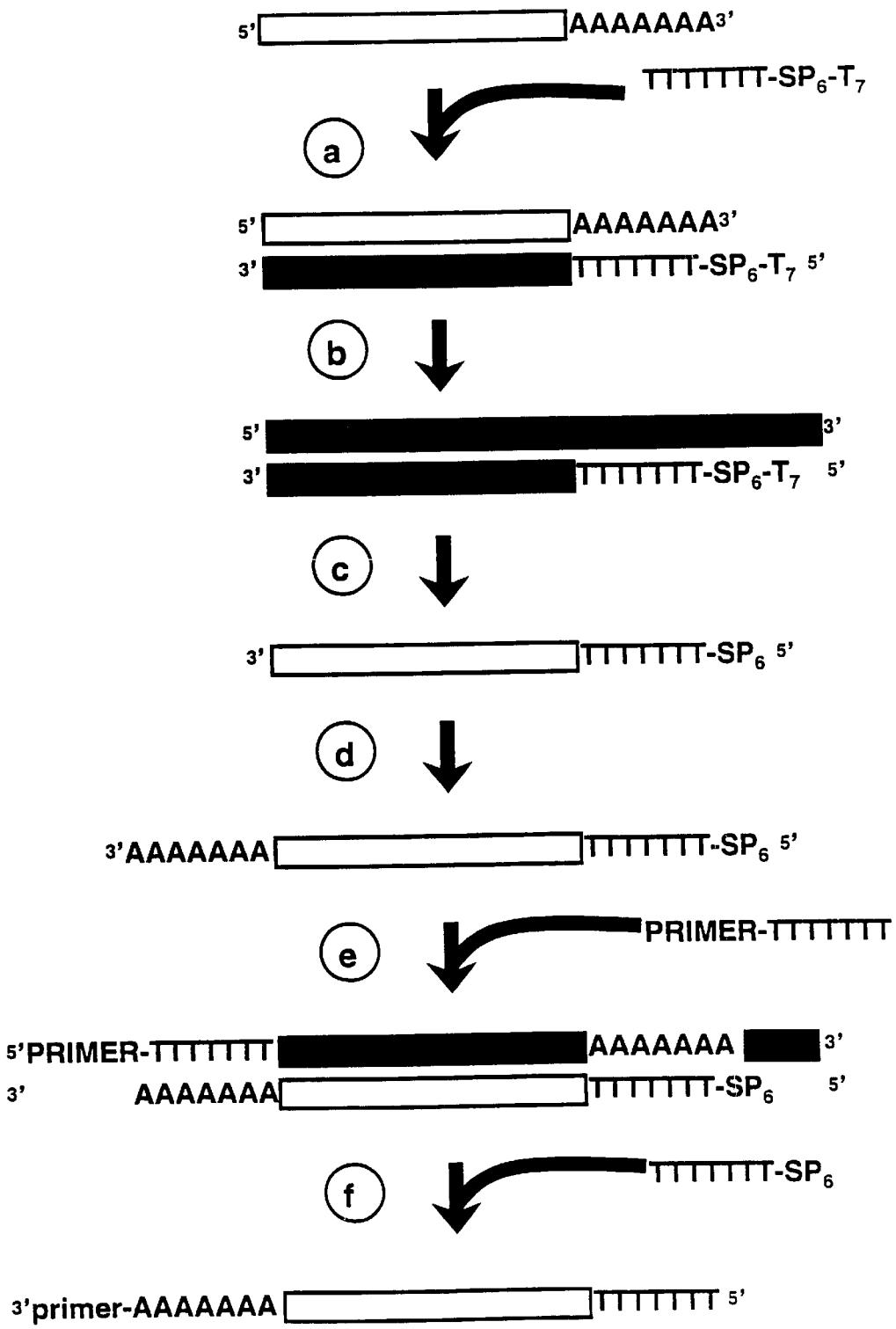
FIG. 4 is a schematic of an alternative embodiment of a preferred mRNA amplification method.

Another embodiment involves the incorporation of additional sequences during certain synthesis steps. These sequences allow, for example, for the PCR amplification of the amplified RNA, for direct second-round amplification without synthesizing a full second strand cDNA, etc. This embodiment is diagramed in FIG. 4:

(a) This is step (a) of FIG. 3, except that the primer for first strand cDNA synthesis also includes a promoter site for a different RNA polymerase (shown with $SP_6$; $T_3$ RNA polymerase site is also possible) between the poly(T) and the $T_7$ sequences;

(b) This is step (b) of FIG. 3;

(c) This is step (c) of FIG. 3, except that the aRNA now has an RNA polymerase site at its 5' end;

(d) This is step (d) of FIG. 3;

(e) This is step (e) of FIG. 3, except that the oligonucleotide used for priming first strand cDNA synthesis also has an additional sequence at its 5' end suitable for use as a priming site during polymerase chain reaction (PCR). Note also that the $SP_6$ or $T_3$ RNA polymerase site has been copied into first strand cDNA. Because this first strand cDNA has unique sequences at both its 5' and 3' ends, it can now be used directly in a PCR reaction for total amplification of all sequences, as an alternative to performing another round of aRNA synthesis;

(f) The first strand cDNA can be used directly for aRNA synthesis by annealing an oligonucleotide incorporating the complementary portion of the $SP_6$ or preferably, the $T_3$ RNA polymerase site. Or, the first strand cDNA can be converted into double-stranded cDNA through second strand synthesis, with aRNA synthesis then following.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for defining a cell type of a cell comprising the steps of:
   (a) amplifying the mRNA of a single cell, of undefined cell type of a heterogenous population of cells;
   (b) probing a comprehensive expression library with the amplified mRNA to define a gross expression profile of the cell;
   (c) comparing the gross expression profile of the cell with a gross expression profile of one or more other cells to define a unique expression profile of the cell, wherein the unique expression profile of the cell provides a marker defining the cell type.

2. A method according to claim 1, wherein step (c) comprises comparing the gross expression profile of the cell with a gross expression profile of a plurality of other cells to define a unique expression profile of the cell.

3. A method according to claim 1, wherein step (c) comprises comparing the gross expression profile of the cell with a plurality of gross expression profiles of each of a plurality of other single cells to define a unique expression profile of the cell.

4. A method according to claim 1, wherein step (c) comprises comparing the gross expression profile of the cell with a plurality of gross expression profiles of each of a plurality of other single cells to define a unique expression profile of the cell, and the plurality of other single cells are derived from a functionally or structurally distinct subpopulation of cells.

5. A method according to claim 4, wherein the subpopulation of cells is tissue-specific.

6. A method according to claim 4, wherein each cell of the subpopulation of cells comprises a genome comprising a mutation.

7. A method according to claim 4, wherein each cell of the subpopulation of cells comprises a genome comprising a mutation, wherein the mutation provides each cell with a common selectable or detectable marker.

8. A method according to claim 4, wherein each cell of the subpopulation of cells comprises a genome comprising a mutation, wherein the mutation is an inserted construct which encodes and provides each cell with a common selectable marker selected from an epitope or a signal-producing protein.

9. A method according to claim 4, wherein each cell of the subpopulation of cells comprises a genome comprising a mutation, wherein the mutation is an inserted construct which encodes and provides each cell a signal-producing protein selected from the group consisting of a green fluorescent protein, a galactosidase and an externally accessible, cell-surface associated protein.

10. A method according to claim 4, wherein each cell of the subpopulation of cells comprises a genome comprising a mutation, wherein the mutation is an inserted construct which encodes and provides each cell with a common selectable marker selected from the group consisting of an epitope or a signal-producing protein, and the inserted construct further encodes and provides each cell an internal ribosome entry sequence and the construct is inserted into a target gene downstream of the stop codon but upstream of the polyadenylation signal in the last exon of the target gene, such that the internal ribosome entry sequence provides a second open reading frame within a transcript of the target gene.

11. A method according to claim 4, wherein each cell of the subpopulation of cells comprises a genome comprising a mutation, wherein the mutation is an inserted construct which encodes and provides each cell with a common selectable marker selected from an epitope or a signal-producing protein, and the subpopulation is isolated by flow cytometry.

12. A method according to claim 1, wherein the library is a cDNA library.

13. A method according to claim 1, wherein the library is normalized or subtracted.

14. A method according to claim 1, wherein the library comprises a high density ordered array of immobilized nucleic acids.

15. A method according to claim 1, wherein the mRNA is amplified by a method comprising the steps of adding a known nucleotide sequence to the 3' end of a first RNA having a predetermined sequence at the 5' end to form a second RNA and reverse transcribing the second RNA to form a cDNA.

16. A method according to claim 1, wherein the mRNA is amplified by a method comprising the steps of adding a predetermined nucleotide sequence to the 3' end of a first RNA having a predetermined sequence at the 5' end to form a second RNA and reverse transcribing the second RNA to form a cDNA and wherein the cDNA is single-stranded and converted to a double-stranded cDNA by a method comprising the steps of contacting the RNA with a denaturant and contacting the single-stranded cDNA with a DNA polymerase and an oligonucleotide primer comprising a sequence complementary to the 3' end of the single-stranded cDNA and an RNA polymerase promoter, whereby the DNA polymerase initiates the conversion at a noncovalently joined duplex region of the 3' end of the single-stranded cDNA and the oligonucleotide primer.

17. A method according to claim 1, wherein the mRNA is amplified by a method comprising the steps of adding a known predetermined nucleotide sequence to the 3' end of a first RNA having a predetermined sequence at the 5' end to form a second RNA and reverse transcribing the second RNA to form a cDNA and wherein the cDNA is single-stranded and converted to a double-stranded cDNA by a method comprising the steps of contacting the RNA with a denaturant and contacting the single-stranded cDNA with a DNA polymerase and an oligonucleotide primer comprising a sequence complementary to the 3' end of the single-stranded cDNA and an RNA polymerase promoter comprising SEQ ID NO:1 joined to an upstream flanking sequence of about 3 to 100 nucleotides, whereby the DNA polymerase initiates the conversion at a noncovalently joined duplex region of the 3' end of the single-stranded cDNA and the oligonucleotide primer.

18. A method according to claim 1, wherein the mRNA is amplified by a method comprising the steps of adding a predetermined nucleotide sequence to the 3' end of a first RNA having a predetermined sequence at the 5' end to form a second RNA and reverse transcribing the second RNA to form a cDNA and wherein the mRNA is amplified by a method comprising the steps of adding a known nucleotide sequence to the 3' end of a first RNA having a known sequence at the 5' end to form a second RNA and reverse transcribing the second RNA to form a cDNA and wherein the cDNA is single-stranded and converted to a double-stranded cDNA, and the method further comprises the step of repeatedly transcribing the double-stranded cDNA to form a plurality of third RNAs.

19. A method according to claim 1, wherein the mRNA is amplified by a method comprising the steps of adding a determined nucleotide sequence to the 3' end of a first RNA having a predetermined sequence at the 5' end to form a second RNA and reverse transcribing the second RNA to form a cDNA and wherein the first RNA is made by amplifying a mRNA.

20. A method according to claim 1, wherein the mRNA is amplified by a method comprising the steps of adding a predetermined nucleotide sequence to the 3' end of a first RNA having a predetermined sequence at the 5' end to form a second RNA and reverse transcribing the second RNA to form a cDNA, wherein the first RNA is made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA.

21. A method according to claim 1, wherein the mRNA is amplified by a method comprising a polymerase chain reaction.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

TAATACGACT CACTATAGGG AGA        23

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:2:

TAATACGACT CACTATAGGC GC        22

(2) INFORMATION FOR SEQ ID NO:3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:3:

TAATACGACT CACTATAGGG CGA        23